United States Patent [19]

Greif et al.

[11] 4,375,565
[45] Mar. 1, 1983

[54] LOW-FOAMING, BIODEGRADABLE ALKOXYLATION PRODUCTS TERMINATED WITH GLYCERINE ETHER RADICALS, AND A PROCESS FOR THEIR PREPARATION

[75] Inventors: Norbert Greif, Bobenheim; Erhard Klahr; Wolfgang Trieselt, both of Ludwigshafen, all of Fed. Rep. of Germany

[73] Assignee: BASF Aktiengesellschaft, Ludwigshafen, Fed. Rep. of Germany

[21] Appl. No.: 311,669

[22] Filed: Oct. 15, 1981

[30] Foreign Application Priority Data

Nov. 13, 1980 [DE] Fed. Rep. of Germany ....... 3042823

[51] Int. Cl.$^3$ ..................... C07C 43/03; C07C 43/10
[52] U.S. Cl. .................................. 568/622; 568/618; 252/174.21
[58] Field of Search ................................ 568/622, 618

[56] References Cited

U.S. PATENT DOCUMENTS 2,951,094 8/1960 Hefner et al. ..................... 568/618

Primary Examiner—Howard T. Mars
Attorney, Agent, or Firm—David L. Hedden; Joseph D. Michaels

[57] ABSTRACT

The subject invention relates to compositions of matter having the following structural formula:

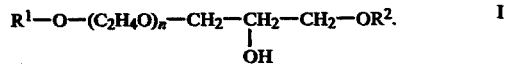

In this formula, $R^1$ represents a $C_8$–$C_{20}$ alkyl radical, $R^2$ stands for a $C_1$–$C_5$ alkyl radical, and n is a number, 4 through 15. These compounds are low foaming and have acceptable biodegradability. They are particularly useful in the formulation of automatic dishwashing detergents.

2 Claims, No Drawings

LOW-FOAMING, BIODEGRADABLE ALKOXYLATION PRODUCTS TERMINATED WITH GLYCERINE ETHER RADICALS, AND A PROCESS FOR THEIR PREPARATION

BACKGROUND OF THE INVENTION

1. Field of the Invention

The invention relates to alkoxylation products having terminal hydroxyl groups which are blocked with glycerine ether radicals. These products are highly biodegradable and are low foaming. The invention further relates to a process for their preparation.

2. Description of the Prior Art

In our mechanized societies, automatic washing processes are primarily used for cleaning dishes and other objects made of glass, china, ceramics or metal. Dishwashing detergents containing specific surface-active compounds are used for this purpose. These detergents must be low foaming for proper functioning of the dishwashers. Too much foaming, caused by the movement of the washing fluid in the machines, results in problems since the foam reduces the cleaning power of the washing fluid being sprayed upon the materials to be cleaned and may cause the machine to overflow.

Compounds generally referred to as ethylene oxide-propylene oxide block polymers, as described in U.S. Pat. No. 2,674,619, represent an important class of non-ionic surfactants used to reduce the foaming of automatic dishwashing detergents. These surfactants are characterized by their low foaming properties and good dispersing capacity. However, they also have a low wetting capacity and their biodegradability is far below 80 percent.

Low-foaming nonionic surfactants which are produced by reaction of a maximum of 1.5 moles butylene oxide with a higher alkanol ethoxylate containing 4 to 10 moles of ethylene oxide per higher alkanol are described in German Published Application No. 1,814,439. It has, however, been determined that these surfactants are not yet satisfactory with respect to their foam inhibiting properties, especially when the washing fluid contain high protein content.

It is well known that the formation of foam can be inhibited by the effects of the higher alkylene oxides such as propylene and/or butylene oxide upon ethoxylated alcohols. This effect is increased as the alkylene oxide content is increased. However, increasing the alkylene oxide content reduces the biodegradability. Thus, for instance, the report of the Sixth International Congress for Surface-Active Materials of Sept. 11–15, 1972 in Zurich by W. K. Fischer of the Henkel KGaA Company (see Vol. 3, page 746, and FIG. 9) explains that ethoxylated $C_{12}$ to $C_{20}$ fatty alcohols with 2 moles of butylene oxide as end groups have a biodegradability which the bottle test listed in this literature reference indicates to be absolutely unsatisfactory.

Although it is known from the monograph, *Catalysts, Surfactants and Mineral Oil Additives,* page 149, column 2, paragraph 2, edited by J. Falbe and U. Hasserodt, (George Thieme Publishers, Stuttgart 1978), that alkoxylation groups may be reacted with glycidyl ethers to prepare products which are useful in detergents because of their low foaming tendencies, this reference says nothing about specific representatives of this product class and no statements are made concerning their biodegradability.

Such compounds which are the propoxylation products of long-chained alcohols which were reacted with a long-chained glycidyl ether, are also described in German Published Application No. 2,225,318. However, they are not water soluble and are used as defoamers in paper coating materials. Moreover, these compounds are not biodegradable.

SUMMARY OF THE INVENTION

The subject invention relates to compositions of matter having the following structural formula:

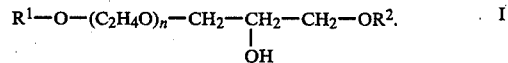

In this formula $R^1$ represents a $C_8$–$C_{20}$ alkyl radical, $R^2$ stands for a $C_1$–$C_5$ alkyl radical, and n is a number, 4 through 15. These compounds are low foaming and have acceptable biodegradability. They are particularly useful in the formulation of automatic dishwashing detergents.

DESCRIPTION OF THE PREFERRED EMBODIMENT

In order to prepare the compositions of the subject invention, aliphatic alcohols having 8 to 20 carbon atoms, or alcohol mixtures, are ethoxylated with 4 to 15 moles of ethylene oxide per mole of alcohol according to well-known methods. The ethoxylation product is subsequently reacted with epichlorohydrin in the presence of an acid catalyst. Thereafter, the reaction mixture is reacted with a $C_1$–$C_5$ aliphatic alcohol in the presence of alkaline catalysts. The specific ingredients will now be described in detail.

Alcohols having 8 to 20 carbon atoms which may be used may be branched or straight chained with straight chained or only slightly branched being preferred. Specific examples include octanol, nonanol, decanol, dodecanol, tetradecanol, hexadecanol, and oxadecanol (stearyl alcohol) as well as their mixtures. Particularly preferred are those which were obtained by the Ziegler or the Oxo synthesis. These are mixtures containing 9/11, 13/15 or 16/18 (oxo synthesis) carbon atoms. The alcohol mixtures obtained by the Ziegler synthesis containing 8/10, 10/12, 12/16 or 16/20 alkyl groups are just as suitable. Particularly advantageous is the $C_{10}/C_{12}$ cut of the alcohol fraction obtained by the Ziegler synthesis.

The ethoxylation of these alcohols or alcohol mixtures is part of the current state of the art and does not require further explanation. The alkoxylation is carried out with 4 to 15, preferably 5 to 11 moles of ethylene oxide per mole of alcohol.

The ethoxylates are subsequently reacted with epichlorohydrin in the presence of acid catalysts. Molar quantities of epichlorohydrin are appropriately used, that is, the mole ratio of ethoxylate to epichlorohydrin should be 1:1. However, slight excesses of epichlorohydrin may also be used, that is a mole ratio of 1:1.5, may also be selected. Suitable "acid catalysts" under the reaction conditions are nonoxidizing mineral acids such as sulfuric acid, perchloric acid and particularly Lewis acids such as $BF_3$-etherate or antimony pentachloride which are used in quantities of 0.1 to 10 percent by weight relative to the weight of the ethoxylate. The reaction requires temperatures of 50° C. to 120° C., preferably 70° C. to 110° C. and generally requires 0.5 hour to 10 hours, preferably 1 hour to 5 hours.

Since it is not necessary to isolate the intermediate product, the reaction solution is then mixed with a primary or secondary $C_1$–$C_5$ alkanol in the presence of an alkaline catalyst. "Alkaline catalysts" are understood to be, for instance, alkali hydroxides such as sodium hydroxide, potassium hydroxide, earth alkali hydroxides such as calcium hydroxide or barium hydroxide, or alkali carbonates such as soda or potash.

$C_1$ to $C_5$ alkanols include, for instance, methanol, ethanol, n- or isopropanol, n- or sec.-butanol, of which n-propanol and n-butanol are preferred. They are used at least in molar ratios relative to the reaction product of the ethoxylate and epichlorohydrin preferably with a 4 to 5 times excess. The reaction temperature may range from 70° C. to 130° C. and the reaction time may range from 3 hours to 10 hours.

The surfactants are obtained after neutralization of the excess alkaline catalyst, filtration of the resultant precipitating salt, and the distillative separation of the excess alcohol.

The resultant products may be characterized, for instance, by their cloud point and their OH number. They meet the regulations published in the Federal Gazette, Part 1, pages 244 et seq. on Jan. 30, 1977, concerning biodegradability as determined by the configuration test.

The new surfactants are used in industrial washing and cleaning processes which may cause particularly pronounced foaming as a result of the high amount of turbulence.

The examples which follow will provide further details related to the practice of this invention.

EXAMPLES

Generally, the subject surfactants are prepared by reacting 1 mole of alkanol in an autoclave with the desired mole quantity of ethylene oxide at 120° C. in the presence of 1 gram of potassium hydroxide. After neutralizing the alkaline catalyst with sulfuric acid, the ethoxylation product is mixed dropwise with 1 mole of epichlorohydrin (92.5 grams) in the presence of 2 grams of $BF_3$-etherate at a temperature of 70° C. to 80° C. The reaction is completed while stirring at 100° C. within 4 hours. Without isolating the intermediate product, 5 moles of $C_1$–$C_5$ alkanol are subsequently added. Then, 41 grams of powdered sodium hydroxide are introduced in portions at 25° C. to 35° C.; the reaction mixture is left at the referenced temperature for 1 hour and is heated to 100° C. for 5 hours. Subsequently, the sodium hydroxide is neutralized with acetic acid, the precipitated salt is removed by filtration, and the excess alkanol is removed by distillation under reduced pressure.

EXAMPLE 1

In an autoclave, 130 grams of octanol are reacted with 264 grams of ethylene oxide at 120° C. in the presence of 0.6 gram of potassium hydroxide. After neutralizing the alkaline catalyst with 0.6 gram of 98 percent sulfuric acid, the ethoxylation product is mixed dropwise with 1 mole of epichlorohydrin (96.5 grams) at 75° C. in the presence of 2 grams of $BF_3$-etherate. The reaction is completed while stirring at 100° C. within 4 hours. Without isolating the intermediate product, 160 grams of methanol are subsequently added and 41 grams of powdered NaOH are added by portions at 25° C. to 35° C. The reaction mixture remains at the abovereferenced temperature for 1 hour and is heated for 5 hours under reflux cooling.

Subsequently, the excess sodium hydroxide is neutralized with acetic acid, the precipitated salt is removed by filtration and the excess alcohol is removed by distillation at 70° C. under a pressure of 70 millibars. The yield is 450 grams of product having a light yellow color and a water cloud point of 42° C.

EXAMPLE 2

The procedure was as that described under Example 1 but 352.6 grams of n-pentanol were used instead of methanol. The yield is 506 grams of product having a light yellow color and a water cloud point of less than 0° C.

EXAMPLE 3

In an autoclave, 168 grams of a $C_{10}$–$C_{12}$ Ziegler alcohol mixture ($C_{10}$–$C_{12}$-ALFOL ®) are reacted with 391.6 grams of ethylene oxide as described in Example 1 with 1 gram of KOH as catalyst. The material is neutralized with 1 gram of 98 percent sulfuric acid. The ethoxylation product is reacted with 92.5 grams of epichlorohydrin. Then, the addition of 360 grams of n-butanol and sodium hydroxide is carried out as described in Example 1. After stirring for 1 hour at 25° C. to 35° C., the reaction mixture is heated to 100° C. for 5 hours.

Further processing takes place as described under Example 1. The yield is 680 grams of product having a light yellow color and a water cloud point of 19.5° C.

EXAMPLE 4

In an autoclave, 208 grams of $C_{13/15}$ oxoalcohol are reacted with 396 grams of ethylene oxide as described in Example 2 with 1 gram of potassium hydroxide as catalyst. Further reaction and processing follows the guidelines set forth in Example 2 with the n-butanol being replaced by sec.-butanol. The yield is 730 grams of product having a light yellow color and water cloud point of 32.5° C.

EXAMPLE 5

In an autoclave, 208 grams of $C_{13/15}$ oxoalcohol are reacted with 440 grams of ethylene oxide as described in Example 2 with 1 gram of potassium hydroxide as catalyst. Further reaction and processing are carried out as described in Example 2. The yield is 780 grams of product having a light yellow color and a water cloud point of 23.5° C.

EXAMPLE 6

As described in Example 2, 255 grams of tallow fatty alcohol are reacted with 1 gram potassium hydroxide as catalyst and 484 grams of ethylene oxide. The material is neutralized with 1 gram of 98 percent sulfuric acid. The ethoxylation product is reacted with 92.5 grams of epichlorohydrin. The addition of 230 grams of ethanol and sodium hydroxide is carried out as explained in Example 1. After stirring at 25° C. to 35° C. for 1 hour, the reaction mixture is heated for 5 hours under reflux cooling.

Processing is then further carried out as described in Example 1. The yield is 820 grams of product having a light yellow color and a water cloud point of 63.5° C.

EXAMPLE 7

In an autoclave, 255 grams of tallow fatty alcohol are reacted in the same manner as described in Example 5.

After reaction with epichlorohydrin, 352.6 grams of n-pentanol and the sodium hydroxide are added as put forth in Example 1.

After 1 hour at 25° C. to 35° C., the reaction mixture is stirred at 100° C. for 5 hours.

Processing is further carried out as described in Example 1 with the excess n-pentanol being removed by distillation at 80° C. and 50 millibars. The yield is 870 grams of product having a light yellow color and a water cloud point of 52.5° C.

EXAMPLE 8

In an autoclave, 270.5 grams of stearyl alcohol are reacted with 1.5 grams potassium hydroxide as catalyst and 616 grams of ethylene oxide as described in Example 2.

The mixture is neutralized with 1.5 grams of 98 percent sulfuric acid.

The further reaction and processing is carried out as described in Example 1. The yield is 960.5 grams of a product with a light yellow color and a water cloud point of 82.5° C.

Table I which follows provides data on the cloud point (determined in accordance with DIN 97913), foaming power (determined in accordance with DIN 93902) and biodegradability of the surfactants prepared in Examples 1–8. The table also provides such data for comparative surfactants. The table shows that the surfactants of the present invention are much lower foamers than the comparative surfactants, but are still biodegradable.

TABLE I[1]

| Example | Product Description by Ingredients | Cloud Point $H_2O$ DIN 97913 | Foam DIN 93902 | Biodegradability Confirmation Test |
|---|---|---|---|---|
| 1 | Octanol + 6 EO + Epi + methanol | 42° C. | 10 cm | >80% |
| 2 | Octanol + 6 EO + Epi + n-pentanol | <0° C. | 10 cm | >80% |
| * | Octanol + 6 EO | 75° C. | 590 cm | >80% |
| 3 | Alfol$_{10/12}$ + 3.9 EO + Epi + n-butanol | 19.5° C. | 20 cm | >80% |
| * | Alfol$_{10/12}$ + 8.9 EO | 89° C. | 740 cm | >80% |
| 4 | $C_{13/15}$—oxoalcohol + 9 EO + sec-butanol | 32.5° C. | 40 cm | >80% |
| * | $C_{13/15}$—oxoalcohol + 9 EO | 68° C. | 650 cm | >80% |
| 5 | $C_{13/15}$—oxoalcohol + 10 EO + Epi + n-butanol | 23.5° C. | 30 cm | >80% |
| * | $C_{13/15}$—oxoalcohol + 10 EO | 77° C. | 700 cm | >80% |
| 6 | Tallow fatty alcohol + 11 EO + Epi + ethanol | 63.5° C. | 100 cm | >80% |
| 7 | Tallow fatty alcohol + 11 EO + Epi + n-pentanol | 52.5° C. | 110 cm | >80% |
| * | Tallow fatty alcohol + 11 EO | 97° C. | 510 cm | >80% |
| 8 | Stearyl alcohol + 14 EO + Epi + methanol | 82.5° C. | 130 cm | >80% |
| * | Stearyl alcohol + 14 EO | >100° C. | 500 cm | >80% |

[1] In the table, the abbreviation EO is used to designate ethylene oxide and Epi is used to designate epichlorohydrin.
*The asterisk designates comparative examples.

The embodiments of the invention in which an exclusive privilege or property is claimed are defined as follows:

1. A composition of matter having the following structural formula:

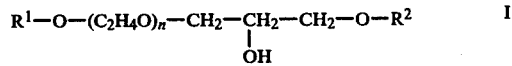

$$R^1-O-(C_2H_4O)_n-CH_2-CH_2-CH_2-O-R^2 \quad \text{I}$$
$$\underset{\text{OH}}{|}$$

wherein $R^1$ is an alkyl group having 8 to 20 carbon atoms, $R^2$ is an alkyl group having 1 to 5 carbon atoms, and n is an integer from 4 to 15.

2. A cogeneric mixture of compounds having the following structural formula:

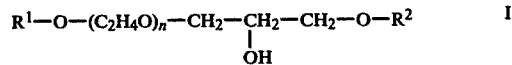

$$R^1-O-(C_2H_4O)_n-CH_2-CH_2-CH_2-O-R^2 \quad \text{I}$$
$$\underset{\text{OH}}{|}$$

wherein $R^1$ is an alkyl group selected from the groups consisting of $C_8$ and $C_{10}$, $C_{10}$ and $C_{12}$, $C_{12}$ and $C_{16}$, $C_{16}$ and $C_{20}$, $C_9$ and $C_{11}$, $C_{13}$ and $C_{15}$, and $C_{16}$ and $C_{18}$, $R^2$ is an alkyl group having 1 to 5 carbon atoms, and n is an integer from 4 to 15.

* * * * *